(12) United States Patent
Beard et al.

(10) Patent No.: US 9,974,675 B2
(45) Date of Patent: May 22, 2018

(54) DELIVERY AND DEPLOYMENT SYSTEMS FOR BIFURCATED STENT GRAFTS

(71) Applicant: W. L. Gore & Associates, Inc., Newark, DE (US)

(72) Inventors: Matthew S. Beard, Phoenix, AZ (US); Martin J. Sector, Gilbert, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 178 days.

(21) Appl. No.: 14/675,368

(22) Filed: Mar. 31, 2015

(65) Prior Publication Data

US 2015/0282967 A1 Oct. 8, 2015

Related U.S. Application Data

(60) Provisional application No. 61/975,217, filed on Apr. 4, 2014.

(51) Int. Cl.
*A61F 2/954* (2013.01)
*A61F 2/07* (2013.01)
*A61F 2/06* (2013.01)

(52) U.S. Cl.
CPC ............. *A61F 2/954* (2013.01); *A61F 2/07* (2013.01); *A61F 2002/065* (2013.01)

(58) Field of Classification Search
CPC ....... A61F 2/07; A61F 2/954; A61F 2002/065
See application file for complete search history.

(56) References Cited

U.S. PATENT DOCUMENTS

| | | | |
|---|---|---|---|
| 5,609,627 A * | 3/1997 | Goicoechea | A61F 2/07 128/898 |
| 5,792,144 A | 8/1998 | Fischell et al. | |
| 6,241,758 B1 | 6/2001 | Cox | |
| 6,352,561 B1 | 3/2002 | Leopold et al. | |
| 6,551,350 B1 | 4/2003 | Thornton et al. | |
| 7,435,253 B1 * | 10/2008 | Hartley | A61F 2/07 623/1.11 |

(Continued)

FOREIGN PATENT DOCUMENTS

| | | |
|---|---|---|
| FR | 2 748 197 | 11/1997 |
| WO | 98/53761 | 12/1998 |

(Continued)

OTHER PUBLICATIONS

International Search Report and Written Opinion for PCT/US2015/023874 dated Jul. 8, 2015, corresponding to U.S. Appl. No. 14/675,368, 5 pages.

*Primary Examiner* — Julie A Szpira

(57) ABSTRACT

A system for endoluminal delivery of a medical device, wherein the medical device includes a bifurcated stent graft having a trunk, a first leg and a second leg shorter than the first leg. The system includes a sheath having a tubular wall having a cylindrical inner surface defining a lumen for receiving the stent graft therein to constrain the stent graft toward a delivery configuration suitable for endoluminal delivery, and a generally cylindrical core member extending through the lumen. The core member has a first annular surface for engaging an end of the first leg. The core has a second annular surface for engaging an end of the second leg while at least the end of the second leg remains constrained by the sheath.

2 Claims, 4 Drawing Sheets

(56) References Cited

U.S. PATENT DOCUMENTS

| | | | |
|---|---|---|---|
| 7,550,002 | B2 | 6/2009 | Goto et al. |
| 8,109,983 | B2 | 2/2012 | Gunderson et al. |
| 2004/0230286 | A1 | 11/2004 | Moore et al. |
| 2005/0049609 | A1* | 3/2005 | Gunderson ............. A61F 2/966 606/108 |
| 2007/0050015 | A1* | 3/2007 | O'Brien ................... A61F 2/07 623/1.35 |
| 2008/0132906 | A1 | 6/2008 | Rasmussen |
| 2009/0132026 | A1* | 5/2009 | Martin .................... A61F 2/954 623/1.23 |
| 2010/0049293 | A1 | 2/2010 | Zukowski et al. |
| 2014/0018913 | A1 | 1/2014 | Cartledge et al. |
| 2014/0046317 | A1 | 2/2014 | Truckai et al. |

FOREIGN PATENT DOCUMENTS

| | | |
|---|---|---|
| WO | 2007/025101 | 3/2007 |
| WO | 2008/066917 | 6/2008 |

\* cited by examiner

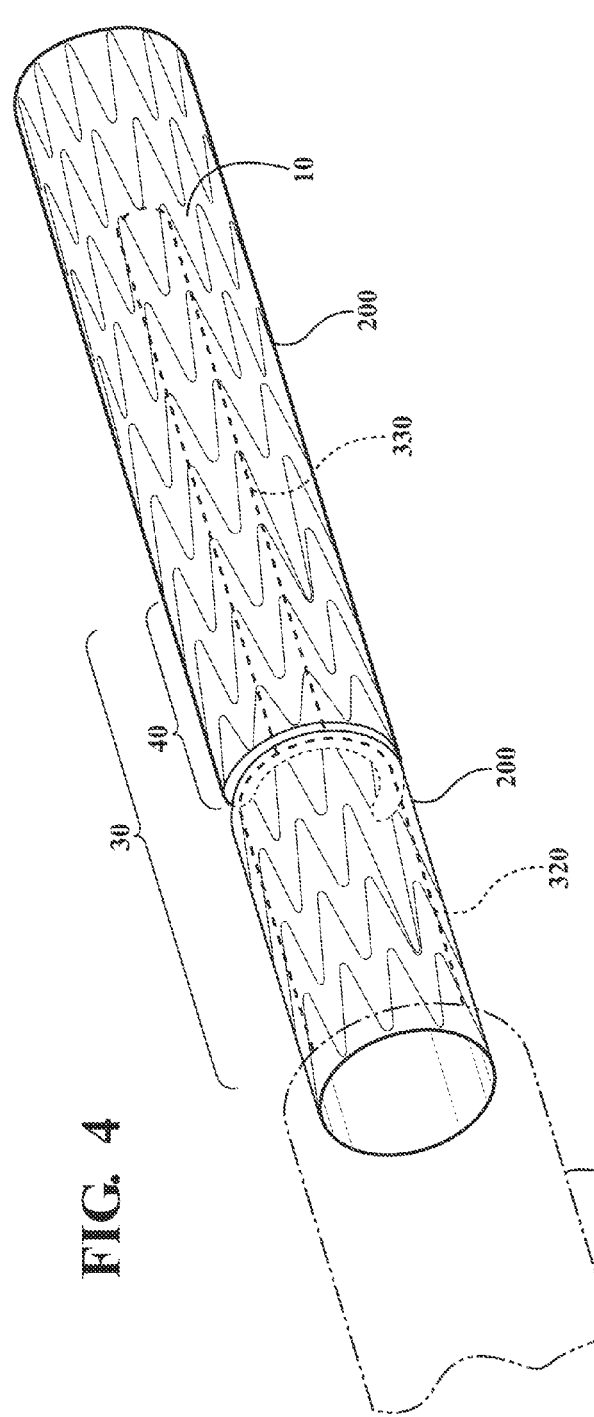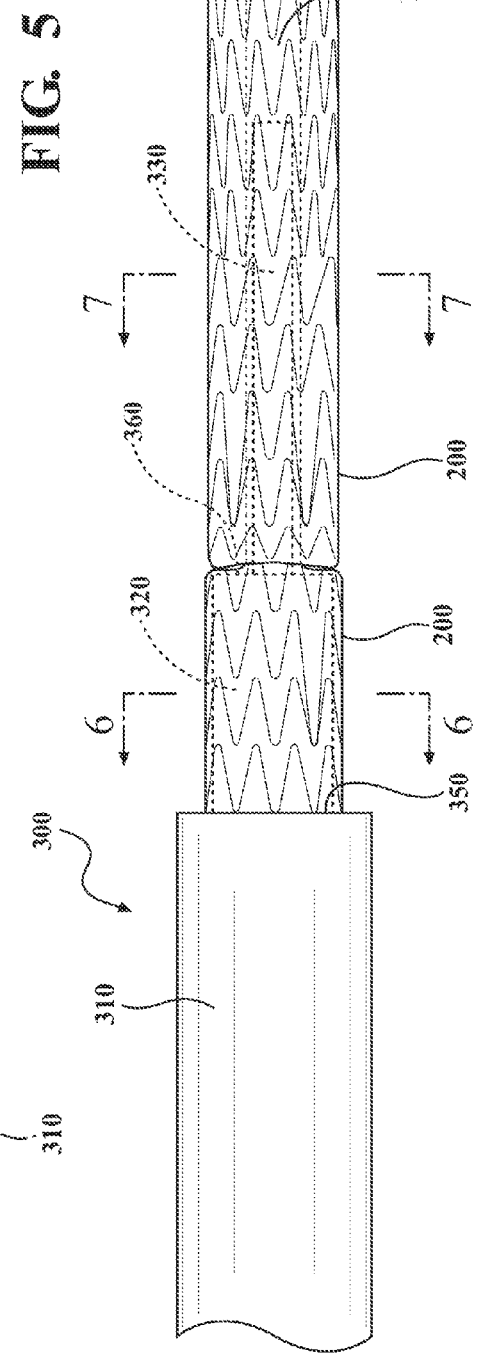

DELIVERY AND DEPLOYMENT SYSTEMS FOR BIFURCATED STENT GRAFTS

BACKGROUND

Field

The present disclosure relates to medical device deployment systems. More particularly, the present disclosure relates to deployment system for bifurcated stent grafts.

Discussion of the Related Art

There is a need for advanced devices, tools, systems and methods used for the endoluminal treatment of aortic diseases. In particular, there remains a need for deployment systems that can accommodate increasingly complex modes of deployment of a device, such as steering, reconstraining, multiple stage deployment, multiple device deployment, while promoting ease of use to the clinician. There also remains a need for increasingly reduced profile delivery mechanisms.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

FIGS. 4-5 illustrate a bifurcated stent graft retained in a delivery configuration by a deployment system in accordance with various embodiments;

DETAILED DESCRIPTION

Figure 1:
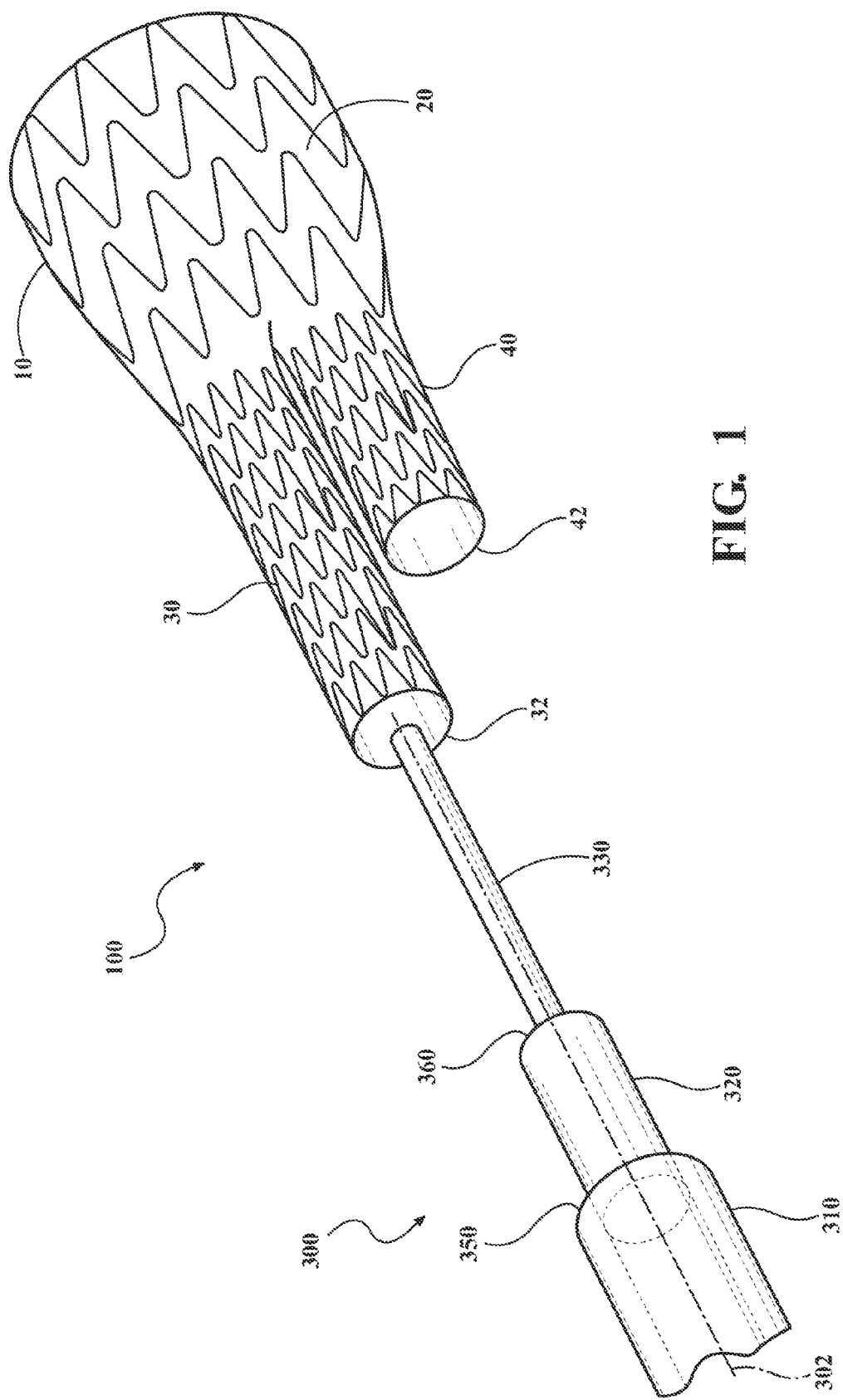
FIGS. 1-3 illustrate a bifurcated stent graft and a portion of a deployment system in accordance with various embodiments.

In various embodiments, a system for endoluminal delivery of a medical device includes a bifurcated stent graft comprising a trunk, a first leg and a second leg, wherein the first leg is longer than the second leg; a sheath having a tubular wall having a cylindrical inner surface defining a lumen for receiving the stent graft therein to constrain the stent graft toward a delivery configuration suitable for endoluminal delivery; and a generally cylindrical core member extending through the lumen, the core member having a first section having a first diameter, a second section having a second diameter smaller than the first diameter, and a third section having a third diameter smaller than the second diameter, the core having an annular first end surface between the first and second sections, and an annular second end surface between the second and third sections, wherein the first and second ends surfaces of the core member engage respective axially spaced apart portions of the stent graft during axial displacement of the sheath with respect to the core member.

Referring to FIGS. 1-8, for example, a delivery system for delivery of a bifurcated stent graft 10 is generally indicated at 100. As shown, the stent graft 10 includes a trunk 20, a first leg 30 and a second leg 40, wherein the first leg 30 is longer than the second leg 40. The delivery system 100 includes a sheath 200 having a tubular wall 210. The tubular wall includes an outer surface 212 and an opposite inner surface 214 defining a lumen 216. The lumen 216 is configured to receive the stent graft 10 therein to constrain and maintain the stent graft 10 in a delivery configuration suitable for endoluminal delivery to a vascular treatment site.

The delivery system 100 includes a core member 300. The core member 300 has a longitudinal axis 302 and through the lumen 216 of the sheath 200. The core member 300 includes a first section 310 having a first diameter. The core member 300 includes a second section 320 having a second diameter smaller than the first diameter. The core member 300 includes a third section 330 having a third diameter smaller than the second diameter.

The core member 300 includes an annular first end surface 350 between the first 310 and second 320 sections. The first end surface 350 can be substantially normal to the longitudinal axis 302 of the core member 300. Similarly, the core member 300 includes an annular second end surface 360 between the second 320 and third 330 sections. The second end surface 360 can be substantially normal to the longitudinal axis 302 of the core member 300.

Figure 2:
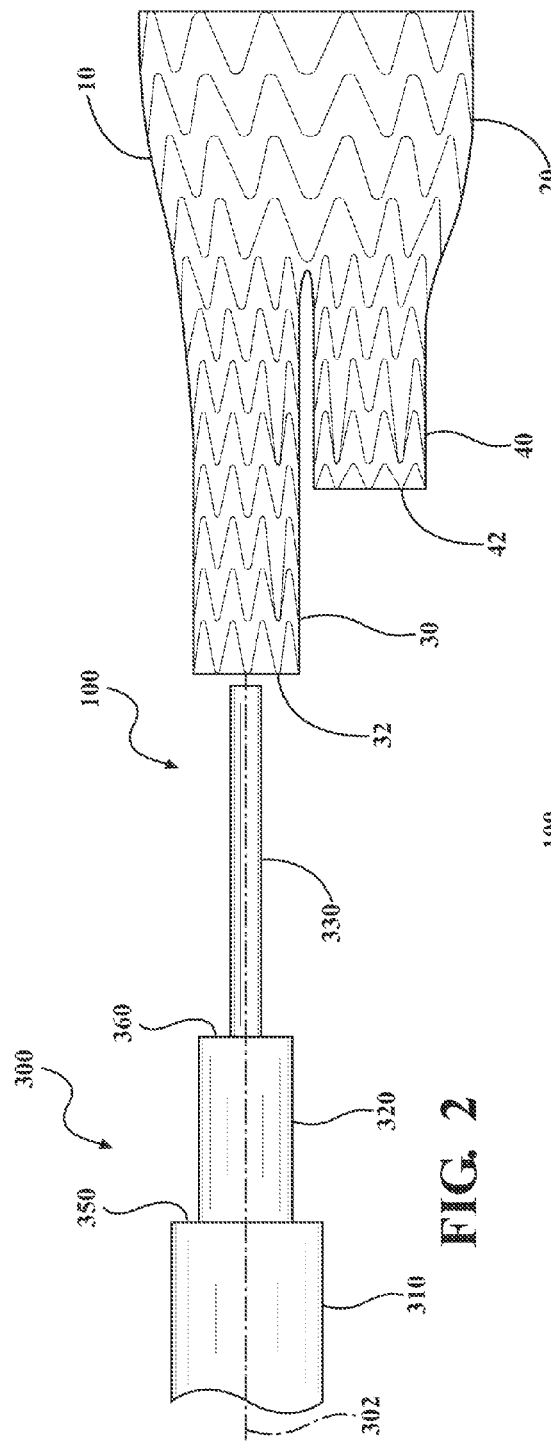
Figure 3:
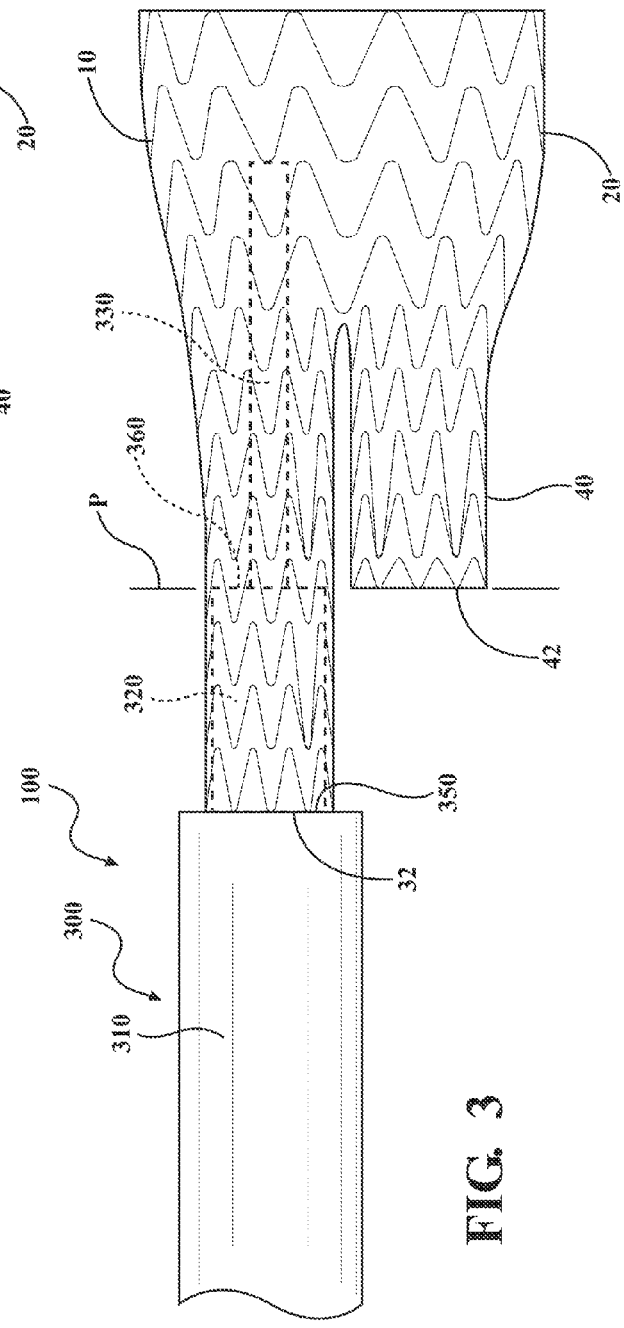
Figure 6:
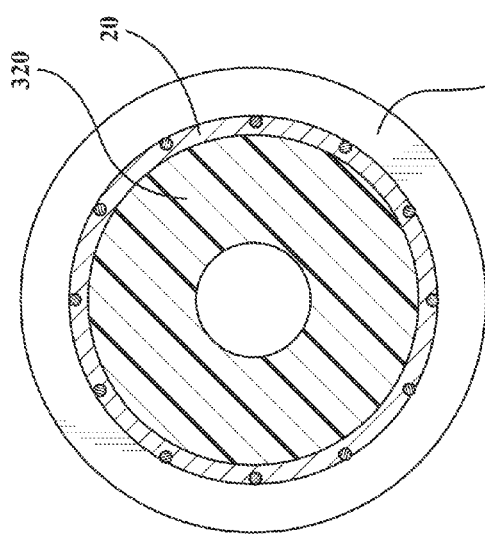
FIGS. 6-7 are cross sectional views of the bifurcated stent graft and deployment system as taken along planes indicated at 6-6 and 7-7 in FIG. 5, respectively.
Figure 7:
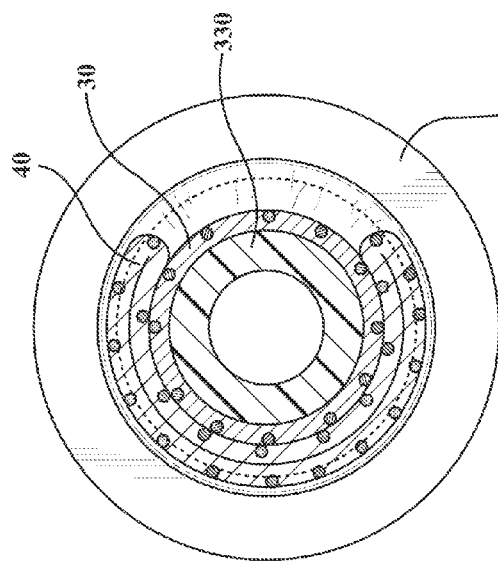
Figure 8:
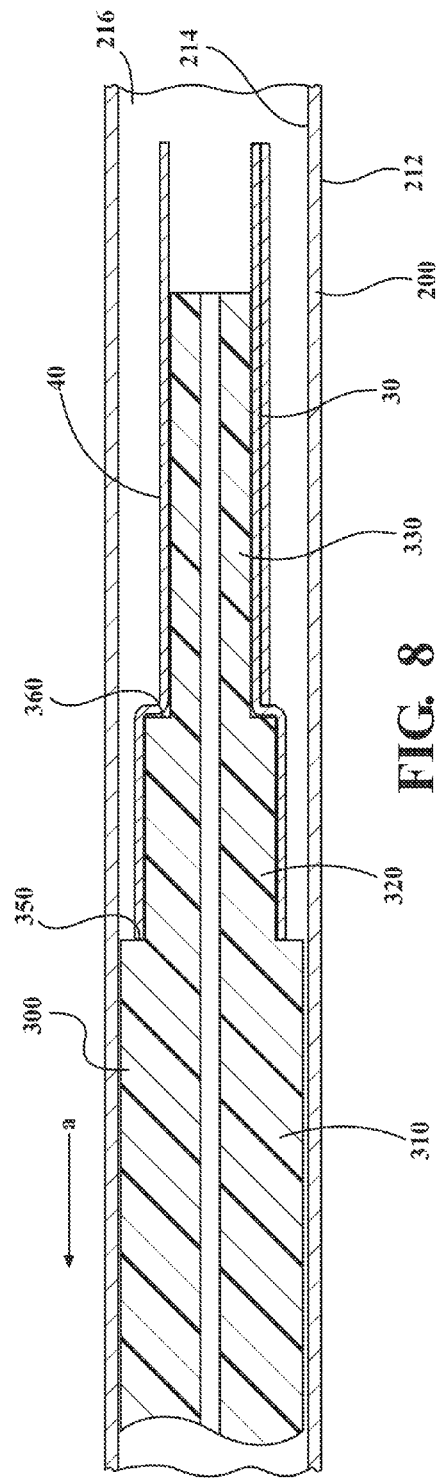
FIG. 8 is a longitudinal cross sectional view of the bifurcated stent graft and deployment system in FIG. 5.

During assembly, the core member 300 can be inserted through the first leg 30 of the stent graft 10, as shown in FIG. 1, until a terminal end 32 of the first leg 30 abuts the first end surface 350, as shown in FIGS. 2 and 3. A terminal end 42 of the second leg 40 of the stent graft 10 is generally aligned axially with the second end surface 360, as indicated at plane "P" in FIG. 3.

With the stent graft 10 mounted in the configuration shown in FIG. 3, the stent graft 10 is then compacted generally radially onto the core member 300 and retained in the delivery configuration by the sheath 200, as shown in FIGS. 4-8. As best shown in the cross sectional view of FIG. 7 (taken along the plane indicated at 7-7 in FIG. 5), the second leg 40 is compacted along a portion of a circumference of the third section 330, while the first leg 30 is compacted and generally co-axially aligned with the third section 330.

By this arrangement, the second leg 40 adds column strength to the stent graft 10 along the core member 300 to help prevent axial crumpling of the stent graft 10 during axial displacement of the sheath 200 relative to the core. Thus, during deployment of the stent graft 10, the sheath 200 is displaced axially along a direction, generally indicated by arrow "a" in FIG. 8, relative to the core member 300. Abutment between the terminal ends 32 and 42 of the first 30 and second 40 legs, respectively, and the first 350 and second 360 end surfaces prevents axial displacement of the stent graft 10 due to friction between the stent graft 10 and the sheath 10 as the sheath 10 is displaced. The enhanced column strength of the compacted stent graft along the third section 330 of the core member 300 also helps to resist axial crumpling the stent graft also due to friction between the stent graft 10 and the sheath 10 as the sheath 10 is displaced relative to the core member 300.

Axial displacement of the sheath 10 relative to the core member 300 allows outward expansion of the stent graft 10 from the delivery configuration. Optionally, secondary sheaths or constraining sleeves can be utilized to limit expansion of the stent graft to an intermediate configuration larger than the delivery configuration and smaller than a fully deployed configuration engaged with vessel walls. Further details of such constraining sleeves can be found, for example, in U.S. Pat. No. 6,352,561 issued to Leopold, et al., U.S. Pat. No. 6,551,350 issued to Thornton, et al., as well as co-pending U.S. Patent Application Publication US 2010/

0049293 A1 (Zukowski et al.), the content of which is incorporated herein by reference in its entirety.

Upon full deployment of the stent graft 10, the core member 300 and sheath 200 can be removed from the treatment site and body of the patient.

It will be apparent to those skilled in the art that various modifications and variations can be made in the present present disclosure without departing from the spirit or scope of the present disclosure. Thus, it is intended that the present present disclosure cover the modifications and variations of this present disclosure provided they come within the scope of the appended claims and their equivalents.

What is claimed is:

1. A medical device delivery system, said system comprising:
    a bifurcated stent graft having a trunk, a first leg and a second leg shorter than the first leg,
    a sheath having a tubular wall having a cylindrical inner surface defining a lumen for receiving the stent graft therein to constrain the stent graft toward a delivery configuration suitable for endoluminal delivery; and
    a generally cylindrical core member extending through the lumen, the core member having a first annular surface and a second annular surface, and a first section having a first diameter and a second section having a second diameter, the second annular surface extending between the first and second sections, the first diameter being larger than the second diameter, wherein a difference between the first diameter and the second diameter is at least twice the sum of a thickness of the first leg and twice a thickness of the second leg, the first and second sections being received within a lumen of the first leg such that the second annular surface is positioned between an end of the second leg and the first annular surface.

2. The system as set forth in claim 1, wherein the first annular surface and the second annular surface are parallel.

* * * * *